(12) United States Patent
Mahmoodi et al.

(10) Patent No.: US 8,325,345 B2
(45) Date of Patent: *Dec. 4, 2012

(54) METHODS AND DEVICES FOR MONITORING OF FRYING OIL QUALITY

(75) Inventors: Abolghassem B. Mahmoodi, Saint Paul, MN (US); Milind Balwant Sabade, Woodbury, MN (US); Ai-Ping Wei, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 261 days.

This patent is subject to a terminal disclaimer.

(21) Appl. No.: 12/920,520

(22) PCT Filed: Mar. 2, 2009

(86) PCT No.: PCT/US2009/035649
§ 371 (c)(1),
(2), (4) Date: Nov. 9, 2010

(87) PCT Pub. No.: WO2009/111372
PCT Pub. Date: Sep. 11, 2009

(65) Prior Publication Data
US 2011/0051141 A1     Mar. 3, 2011

Related U.S. Application Data

(60) Provisional application No. 61/033,487, filed on Mar. 4, 2008.

(51) Int. Cl.
*G01N 21/55* (2006.01)
*G01N 33/03* (2006.01)
*G01N 33/26* (2006.01)

(52) U.S. Cl. ....... 356/445; 356/318; 436/61; 250/458.1; 422/68.1

(58) Field of Classification Search .................. 356/318, 356/319, 326, 445, 317; 250/458.1, 459.1, 250/461.1, 461.2; 436/60, 61; 422/69, 68.1, 422/420
See application file for complete search history.

(56) References Cited

U.S. PATENT DOCUMENTS

| | | | |
|---|---|---|---|
| 4,654,309 A | 3/1987 | Mlinar et al. |
| 4,793,977 A | 12/1988 | Morris |
| 5,055,410 A | 10/1991 | Blumenthal et al. |
| 5,472,878 A | 12/1995 | Lewis et al. |
| 5,569,608 A | 10/1996 | Sommer |

(Continued)

FOREIGN PATENT DOCUMENTS

DE     21 21 188     11/1972

(Continued)

OTHER PUBLICATIONS

U.S. Appl. No. 60/883,868; Wei, et al.; filed Jan. 8, 2007.

(Continued)

*Primary Examiner* — Sang Nguyen
(74) *Attorney, Agent, or Firm* — Kenneth B. Wood

(57) ABSTRACT

Herein are disclosed methods and devices for evaluating the quality of oils (e.g., cooking oil or flying oil). The methods can provide an indication of the free fatty acid content of the oil. The methods use an optical interrogation device to provide an indication of free fatty acid based on quantitative measurements of optical reflectance from test zones on a sampling substrate.

20 Claims, 7 Drawing Sheets

U.S. PATENT DOCUMENTS

| | | | |
|---|---|---|---|
| 5,656,810 | A | 8/1997 | Alfano et al. |
| 5,712,165 | A | 1/1998 | Alvarez et al. |
| 5,818,731 | A | 10/1998 | Mittal et al. |
| 6,127,185 | A * | 10/2000 | Melton et al. ............. 436/60 |
| 6,436,713 | B1 * | 8/2002 | Onwumere et al. ......... 436/56 |
| 6,717,667 | B2 | 4/2004 | Abraham et al. |
| 6,826,424 | B1 | 11/2004 | Zeng et al. |
| 6,867,051 | B1 | 3/2005 | Anderson et al. |
| 7,118,713 | B2 | 10/2006 | Brock et al. |
| 7,132,079 | B2 | 11/2006 | Onwumere et al. |
| 7,136,155 | B2 | 11/2006 | Kong et al. |
| 2003/0064423 | A1 | 4/2003 | Gordon |
| 2003/0119202 | A1 | 6/2003 | Kaylor et al. |
| 2005/0221504 | A1 | 10/2005 | Petruno et al. |
| 2006/0142947 | A1 | 6/2006 | Robrish et al. |
| 2007/0134751 | A1 | 6/2007 | Petrich et al. |
| 2007/0187617 | A1 | 8/2007 | Kong et al. |
| 2007/0279620 | A1 | 12/2007 | Robrish |

FOREIGN PATENT DOCUMENTS

| | | |
|---|---|---|
| EP | 1 326 074 | 7/2003 |
| WO | WO 88/01741 | 3/1988 |

OTHER PUBLICATIONS

Product Literature: 3M Food Service Business, "3M™ Shortening Monitor," 1999, 2 pgs.

Mlinar, J.W., "Paper strips containing modular reaction cells", Sensors and Actuators, vol. 8, No. 3, Nov. 1985, pp. 181-186.

Steinberg, "Chromogenic radical based optical sensor membrane for screening of antioxidant activity", Talanta, vol. 71, No. 4, Feb. 24, 2007, pp. 1782-1787.

Extended European Search Report, PCT/US2009/035649, Oct. 31, 2011, 2 pages.

* cited by examiner

METHODS AND DEVICES FOR MONITORING OF FRYING OIL QUALITY

Cross Reference to Related Applications

This application is a national stage filing under 35 U.S.C. 371 of PCT/US2009/035649, filed Mar. 2, 2009, which claims priority to U.S. Provisional Application No. 61/033487, filed Mar. 4, 2008, the disclosure of which is incorporated by reference in its/their entirety herein.

BACKGROUND

When oils (e.g. cooking oil, frying oil, fat, shortening, etc.) are exposed to high temperatures, particularly in the presence of oxygen and/or water, oxidative reactions can take place that result in degradation of the oils. Thus, oil quality is often monitored in restaurant kitchens, so as to determine whether the oil is still suitable for use.

A parameter often used to evaluate oil quality is the free fatty acid content of the oil. Mlinar and Neumayer, for example, disclose in U.S. Pat. No. 4,654,309 an article for testing liquid for free fatty acid content. An organic liquid to be tested is contacted with the article and any color change in the article after the passage of sufficient time is observed.

SUMMARY

Herein are disclosed methods and devices for evaluating the quality of oils (e.g., cooking oil or frying oil). The methods can provide an indication of the oil quality based on the free fatty acid content of the oil. The methods are advantageous in using an optical interrogation device to provide an indication of oil quality based on quantitative measurements of optical data as described herein, which may provide an improvement over methods that rely on subjective measurements (e.g. visual inspection).

The methods are also advantageous in not requiring the removal of a large sample from the oil supply to be evaluated, nor do the methods require the temporary insertion of an interrogation device, or the permanent placement of such a device, into the oil.

The methods utilize a sampling substrate and an interrogation device. The sampling substrate has at least one test zone whose optical properties are responsive to the free fatty acid content of the oil. In one embodiment, multiple test zones are provided, and the interrogation device comprises means to interrogate the multiple test zones and receive signals therefrom. The device can be further configured to provide an indication of the oil quality in terms of the free fatty acid content of the oil, based on the signals received from the multiple test zones.

In one embodiment, the optical property of the test zone that is responsive to the free fatty acid content of the oil, is an absorptive/reflective property. In a specific embodiment, the optical property is reflectance. In one embodiment, this arrangement is achieved by providing an acid-base indicator in the test zone.

The methods disclosed herein provide an indication of oil quality based on the amount (e.g. concentration) of free fatty acid in the oil. The indication can be an actual numerical value of the concentration of free fatty acid; or, it can be a parameter that, while not directly equal to the actual numerical value, is associated with the value and can serve to allow the user to ascertain the quality of the oil (e.g., determine whether the oil is still suitable for use).

Thus in one aspect, herein is disclosed a method of evaluating the quality of frying oil, the method comprising the steps of: providing frying oil that potentially comprises free fatty acid content; providing an oil-absorbent sampling substrate, wherein the sampling substrate contains a plurality of test zones, wherein each test zone is responsive to free fatty acid; contacting the oil with the sampling substrate such that a sample of the oil is brought into contact with at least a portion of each of the test zones; directing light onto the plurality of test zones; measuring the amount of light reflected from each test zone; generating signals proportional to the amount of light reflected from each test zone, summing the signals together so as to provide an integrated signal; correlating the integrated signal with the free fatty acid content of the oil; and, reporting an indication of the oil quality of the oil, wherein the indication is associated with the free fatty acid content of the oil.

In another aspect, herein is disclosed a method of evaluating the quality of frying oil, the method comprising the steps of: providing an interrogation device that comprises a plurality of light source/photodetector pairs; providing an oil-absorbent sampling substrate, wherein the sampling substrate contains a plurality of test zones, wherein each test zone is responsive to free fatty acid; providing frying oil that potentially comprises free fatty acid content; contacting the oil with the sampling substrate such that a sample of the oil is brought into contact with at least a portion of each of the test zones; positioning the interrogation device and the sampling substrate such that each light source/photodetector pair is placed in proximity to a test zone, so as to provide a plurality of light source/photodetector/test zone sets; for each light source/photodetector/test zone set, directing light onto the test zone from the light source and measuring reflected light therefrom by the photodetector and generating a signal that is proportional to the measured reflected light; combining the signals from the photodetectors so as to provide a combined signal; correlating the combined signal with the free fatty acid content of the oil based on information stored in the interrogation device; and, reporting an indication of the oil quality of the oil, wherein the indication is associated with the free fatty acid content of the oil.

In still another aspect, herein is disclosed system for evaluating the quality of frying oil, the system comprising: an oil-absorbent sampling substrate, wherein the sampling substrate contains a plurality of test zones, wherein each test zone is responsive to free fatty acid; and, an optical interrogation device that comprises a plurality of light source/photodetector pairs; wherein the interrogation device and the sampling substrate are configured such that each light source/photodetector pair can be placed in proximity to a test zone, so as to provide a plurality of light source/photodetector/test zone sets; wherein the interrogation device and the sampling substrate are further configured such that, for each light source/photodetector/test zone set, each test zone can be optically interrogated by the light source/photodetector pair so as to receive a signal therefrom, without moving the interrogation device and the sampling substrate relative to each other; and, wherein the interrogation device comprises means to combine the signals received from the test zones into a combined signal, means to correlate the combined signal with the free fatty acid content of the oil, and means to report an indication of the oil quality of the oil, wherein the indication is associated with the free fatty acid content of the oil.

DRAWINGS

Figure 1A:
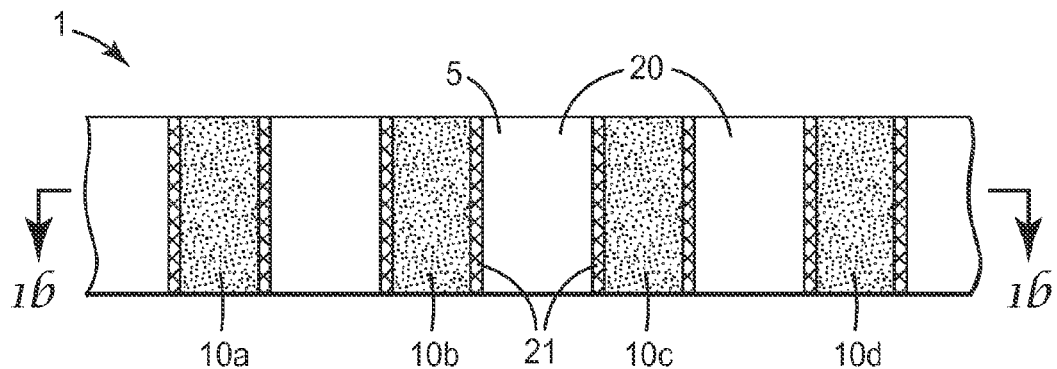
FIG. 1a is a top plan view of an exemplary sampling substrate.

Drawings and elements therein are not to scale unless noted. In the Figures, like reference numerals are used to designate like features throughout. Although terms such as "top", "bottom", "upper", "lower", "over", "under", "front", "back", and "first" and "second" may be used in this disclosure, it should be understood that those terms are used in their relative sense only.

DETAILED DESCRIPTION

Disclosed herein are methods and devices for evaluating the quality of cooking oil (also commonly referred to as e.g. frying oil, vegetable oil, shortening, tallow, grease, etc). The methods rely on a sampling substrate 1 (e.g., a strip, that can be disposed after use) and an interrogation device 30.

Figure 1B:
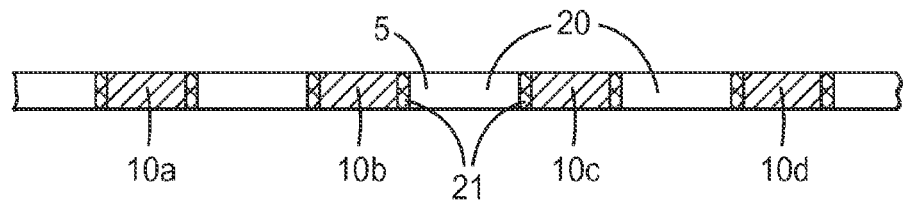
FIG. 1b is a side cross sectional view of an exemplary sampling substrate.

With reference to FIGS. 1a and 1b, sampling substrate 1 is comprised of a porous, oil-absorbent material 5. In this context, the term oil-absorbent means that the material is capable of absorbing oil into the porous interior of the material (e.g., capable of being wetted and/or penetrated by the oil). In various embodiments, material 5 comprises paper, non-woven, open-celled foam, woven fabric, and the like.

Sampling substrate 1 comprises at least one test zone 10 whose optical properties are responsive to the free fatty acid content of an oil sample. In one embodiment, multiple test zones 10a, 10b, etc. are provided, as shown in the exemplary configuration of FIGS. 1a and 1b. In one embodiment, the optical property is a reflectance property, as explained in further detail herein.

In one embodiment, the optical properties of test zone 10 are responsive to the presence of free fatty acid in the oil by virtue of the presence of an acid-base indicator in test zone 10. The indicator may comprise any molecule, or combinations of molecules, that is capable of providing a color change (and hence is capable of displaying an altered optical reflectance at one or more wavelengths) in response to a change in pH. Suitable indicators include for example m-cresol purple, neutral red, thymol blue, phenol red and cresol red.

In one embodiment, test zone 10 also comprises a base compound, which may be any organic or inorganic base compound, including for example sodium carbonate, sodium bicarbonate, and so on. The amount of base compound in each test zone 10 may vary and may be selected in an amount that allows the particular test zone to be responsive to a given amount of acid. Thus in the exemplary configuration of FIGS. 1a and 1b, different amounts of base can be provided in different test zones 10a, 10b, 10c and 10d. In such an arrangement test zone 10a, for example, may be responsive to a different amount of free fatty acid than is test zone 10b (or, alternatively phrased, zones 10a and 10b may respond differently to the same amount of free fatty acid), and so on. In such manner, a sampling substrate 1 can be provided that is responsive to a wide range of free fatty acid concentrations. In various embodiments, at least two, three, four, or five test zones 10 may be used. In various embodiments, zones may be used that are responsive to oil with a content of approximately, e.g., 0.1%-0.5% free fatty acid, 0.5%-1.0% free fatty acid, 1.0%-1.5% free fatty acid, 1.5%-2.0% free fatty acid, 2.0%-2.5% free fatty acid, 2.5%-3.5% free fatty acid, 3.5%-5.0% free fatty acid, or 5.0%-7.0% free fatty acid. If desired, one or more additional test zones may be provided that comprise a similar (or the same) amount of base as does another test zone (i.e., that respond similarly to the same amount of free fatty acid). Such an arrangement may be used, for example, if it is desired to include redundancy in the system.

In one embodiment, test zone 10 also comprises a nonvolatile, pH-neutral humectant that is capable of solubilizing the acid-base indicator and the base compound. Suitable humectants, for example, include dihydroxy aliphatic polyethylene glycol compounds such as those available from Dow Chemical under the designation Carbowax 200, Carbowax 400, and Carbowax 600, and Carbowax 1500.

Without being limited by theory or mechanism, it is postulated that the ability of a test zone 10 to display a change in optical reflectance in response to the amount of free fatty acid in an oil sample, is due to the fact that when the oil sample is brought into contact with the indicator/base/humectant mixture, some or all of the acidic components that may be present in the oil sample may partition into the indicator/base/humectant mixture and affect the acid-base balance thereof, such that the acid-base indicator displays an altered optical absorbtion/reflection property. It is noted herein that the indicator/base/humectant mixture may or may not form a true aqueous solution (depending, for example, on the amount of adventitious water that may be present in the system), since all that is required is that the acid-base indicator be present in such a condition as to be able to respond to the presence of an acidic component.

In one embodiment, the at least one test zone 10 is formed on sampling substrate 1 by mixing the humectant, base compound, and the acid-base indicator (and optionally, volatile solvent such as water or organic solvent) to provide an impregnant mixture, impregnating selected regions of sampling substrate 1 with the impregnant mixture (e.g. by coating, dipping, etc.) such that the impregnant mixture penetrates into (impregnates) the interior of porous material 5 of sampling substrate 1, and allowing sampling substrate 1 to dry (if necessary).

Multiple test zones 10 may be used, and may comprise discrete zones (i.e. they may be physically separated by areas 20 that are not test zones 10). For example, if multiple zones are used (e.g., that differ in their concentration of base compound), it may be useful to minimize the chance of the respective impregnant mixtures migrating (e.g., by wicking laterally through the porous material 5 of sampling substrate 1) so as to encounter each other. Thus in one embodiment, impregnant mixtures are deposited sufficiently far apart to leave areas 20 (which do not contain impregnated materials) therebetween.

In a further embodiment, at least a portion 21 of selected area or areas 20 of sampling substrate 1 can be treated (prior to impregnating sampling substrate 1 with impregnant mixture) so as to minimize or prevent migration of the impregnant mixture. Such barrier treatments can be applied to the surface of sampling substrate 1 and/or to the interior of sampling substrate 1 (i.e., to the interstitial surfaces of porous material 5 that comprises substrate 1), and may include, for example, plasma treatment, vapor deposition, and the like, in a manner that serves to decrease the surface energy (i.e. wettability) of the porous material 5.

In a specific embodiment, the barrier treatment comprises depositing (e.g., coating) a barrier material precursor onto one or both major surfaces of sampling substrate 1 and retaining the deposited barrier material thereon. In one embodiment, the barrier material precursor penetrates into the porous interior spaces of the sampling substrate material 5 and coats the interior surfaces thereof. In various embodiments, suitable barrier materials include those materials that (when deposited and solidified) comprise a very low surface energy, e.g. less than 30 dynes/cm, less than 25 dynes/cm, or less than 20 dynes/cm. Suitable materials include silicones, fluorosilicones, and the like.

Such a low surface energy barrier treatment can be provided in certain locations 21 (for example, bordering one or more test zones 10, as in the exemplary arrangement shown in FIGS. 1a and 1b). Such a barrier treatment may serve to minimize the chance of an impregnant mixture migrating out of its desired location during and after the impregnation process. It may also serve to minimize the chance, during testing, of an oil sample migrating from a test zone (e.g. 10a) to a nearby test zone (e.g. 10b), which might compromise the test results.

Thus in one embodiment, methods disclosed herein comprise treating at least one area of a substrate to form a barrier area 21, leaving at least one untreated area on the substrate. An impregnant solution can then be deposited on at least a portion of the untreated area(s), so as to form at least one test zone 10. In one embodiment, at least two areas of the substrate are treated to form barrier areas 21, leaving an untreated area therebetween. An impregnant solution can then be deposited on at least a portion of the untreated area in between the barrier areas 21, so as to form at least one test zone 10. In one embodiment, after the above processes are performed, at least one area remains which is neither treated with a barrier treatment nor impregnated with an impregnant solution.

Methods of making sampling substrates 1 (e.g., with test areas comprising an acid/base indicator, a base compound and a humectant), are described in further detail by Mlinar and Neumayer in U.S. Pat. No. 4,654,309.

Such sampling substrates can be produced in a variety of configurations. For example, while one convenient configuration of sampling substrate 1 is a rectangular strip and while the term strip may be used herein with reference to sampling substrate 1, it is understood that sampling substrate 1 can be in any convenient shape or configuration, such as square, circular, etc. In one embodiment, sampling substrate 1 can be configured to be symmetrical with regard to the front and back major surfaces of the substrate. In such a case, an oil sample can be applied to either or both major surfaces of the substrate, and/or the substrate may be placed with either of the major surfaces of the substrate facing device 30, for optical interrogation of test zones 10.

Sampling substrates 1 can also contain reference zones as discussed later herein, and can also contain one or more marks (i.e., features, as achieved, for example, by printing or laser-marking). Such a mark may be visually detectable by a user, and/or may be detectable by an interrogation device 30 (described in detail later herein). Such marks may be for the convenience of the user in visually observing the position of sampling substrate 1 as the user positions (i.e. aligns) sampling substrate 1 relative to interrogation device 30 such that test zones 10 can be interrogated. Or, such marks may be machine-readable such that interrogation device 30 can use them to provide feedback to the user as to the proper positioning of sampling substrate 1 relative to interrogation device 30.

Such features may allow a user of device 30, or device 30 itself, to detect when a sampling substrate has been incorrectly positioned, e.g., upside down or backwards, relative to device 30. (such features may not be necessary in certain embodiments; for example, features to denote "front" or "back" may not be necessary in the embodiment in which the substrate is symmetrical with regard to the major sides of the substrate). Such features may also be used by the user or the device to confirm that a particular sampling substrate 1 is compatible with device 30; e.g., to confirm that a particular sampling substrate 1 was designed and/or manufactured in accordance with specifications, tolerances, etc., that enable the sampling substrate to be satisfactorily used with device 30.

The methods disclosed herein involve contacting an oil sample with sample substrate 1 such that the oil sample comes into contact with at least a portion of some or all of test zones 10 (this may be done by dipping the sampling substrate 1 in the oil, by depositing the oil sample onto the substrate, and so on). Sampling substrate 1 with an oil sample brought into contact therewith can then be optically interrogated by the use of device 30. By virtue of the presence of the acid-base indicator, test zones 10 may display different optical absorbtive/reflective properties depending on the amount of free fatty acid in the oil sample. Such optical absorbtive/reflective properties include any measurable property relating to the fact that when a material receives incident light, some light may be absorbed, some may be remitted (e.g. reflected), and some may be transmitted. Any such observable property may be used (i.e. measured) in the methods and devices disclosed herein. In one embodiment, the particular measurement that is used is reflectance. In other embodiments, the particular measurement that is used is absorbtion or transmission.

Figure 2:
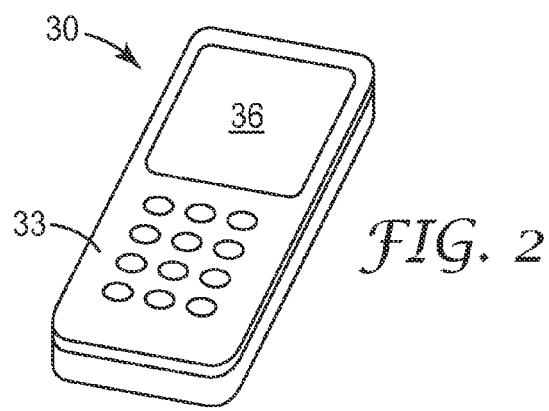
FIG. 2 is a schematic perspective view of an exemplary optical interrogation device.

Thus in summary an optical interrogation operation is performed which involves optically interrogating at least one test zone 10. The operation may be done by directing light on the at least one test zone 10 and measuring the reflected light therefrom. Optical interrogation is performed by an optical interrogation device 30, of which an exemplary design is pictured in FIG. 2. One function of such a device is to generate light to be directed onto test zones(s) 10 for reflectance testing. Thus, with reference to FIG. 3, device 30 comprises at least one light source 31 for directing light onto at least one test zone 10 of sampling substrate 1. In one embodiment, device 30 comprises fewer light sources 31 than sampling substrate 1 comprises test zones 10 (in a particular embodiment, one light source 31 is used). In such an embodiment, at least one light source 31 is used to direct light onto more than one test zone 10. This can be done by using a common light source to simultaneously direct light onto multiple test zones 10. Or, it can be done by directing light from one light source 31 sequentially onto multiple test zones 10, e.g. by moving light source 31 and sampling substrate 10 relative to each other.

In an alternate embodiment, multiple light sources 31 are used to direct light onto multiple test zones 10. In a particular embodiment, the same number of light sources 31 and test zones 10 are used. For example, in the exemplary design shown in FIGS. 1 and 3, device 30 comprises four light sources 31a, 31b, 31c and 31d, and sampling substrate 1 comprises four test zones 10a, 10b, 10c and 10d. In one embodiment, light sources 31 are spatially arranged so as to correspond to the spatial arrangement of zones 10 (i.e., light sources 31 and test zones 10 are aligned such that light can be directed from a light source 31 onto a corresponding test zone 10 without having to move sampling substrate 1 and device 30 relative to each other). For example, test zones 10 may be arranged in a linear format at a given center to center spacing, with light sources 31 arranged in the same format. Light sources 31 can be configured so as to all operate simultaneously or near-simultaneously; or, they be configured to operate in sequence.

Light source 31 may comprise any of a variety of light sources, including bulbs (e.g. incandescent bulbs) and the like. In one embodiment, light source 31 comprises a light-emitting diode (LED), which may be particularly advantageous in the present methods. In various embodiments, an LED can be used that emits light in a particular wavelength range (e.g. green, blue, red, IR, etc.). In a particular embodiment, a white LED is used (i.e., an LED that emits radiation of wavelengths covering at least a substantial portion of the visible spectrum). One exemplary LED that can be used is available from Super Bright LEDs, St. Louis, Mo., under the designation RL5-W5020. In further configurations, different wavelength LEDs can be used as light sources to interrogate different test zones.

Figure 3:
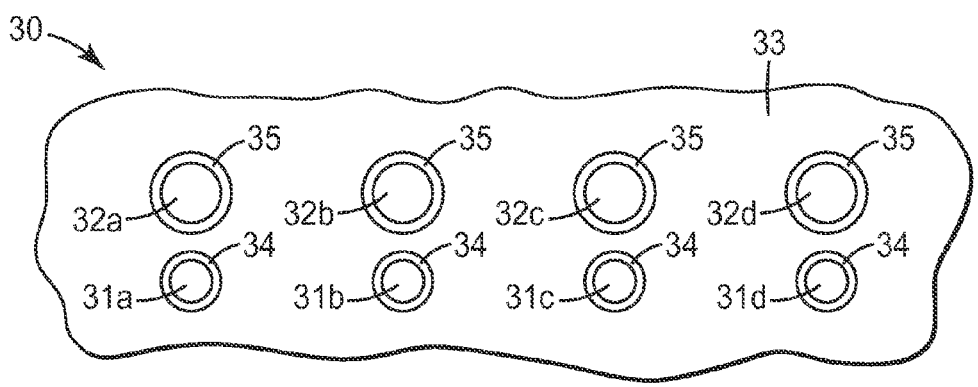
FIG. 3 is a bottom plan view of portion of an exemplary optical interrogation device.

With reference to FIG. 3, device 30 also comprises at least one photodetector 32 for measuring reflected light from at least one test zone 10. In one embodiment, device 30 comprises fewer photodetectors 32 than sampling substrate 1 comprises test zones 10 (in a particular embodiment, one photodetector 32 is used). In such an embodiment, interrogation of the test zones involves using one photodetector to measure light from more than one test zone 10. This can be done, for example, by sequentially measuring light from individual test zones 10.

In an alternate embodiment, multiple photodetectors 32 are arranged to receive light reflected from multiple test zones 10. In a particular embodiment, the same number of photodetectors 32 and test zones 10 are used. For example, in the exemplary design shown in FIGS. 1 and 4, device 30 comprises four photodetectors 32a, 32b, 32c and 32d, and sampling substrate 1 comprises four test zones 10a, 10b, 10c and 10d. In one embodiment, photodetectors 32 are spatially arranged so as to correspond to the spatial arrangement of test zones 10. (e.g., such that light can be received by photodetectors 32 without having to move sampling substrate 1 and device 30 relative to each other).

Photodetector 32 may comprise any of a variety of devices capable of measuring the number of incident photons, including for example a photomultiplier tube, a photovoltaic cell, a charge coupled device, and the like. Photodetector 32 serves to provide a signal (e.g., a voltage) that is proportional to the number of photons detected (e.g., to the intensity or strength of the reflected light received from test zone 10) and that can be further processed by device 30. In one embodiment, photodetector 32 comprises a photodiode. In various embodiments photodetector 32 can be configured to detect light of a specific, relatively narrow wavelength range (for example, the green, blue, red or IR wavelength ranges mentioned above); or, photodetector 32 can be configured to detect light over relatively wide wavelengths. In a specific embodiment, photodetector 32 comprises a photodiode that is configured to detect light over a substantial portion of the visible spectrum, e.g. in the wavelength range of about 400 nm to about 800 nm. In a particular embodiment, the wavelength of light detectable by photodetector 32 is chosen so as to cover substantially the same range as the light emitted by light source 31. One exemplary photodetector that can be used is a photodiode available from Hamamatsu Photonics of Hamamatsu City, Japan, under the designation S9345.

Figure 4:
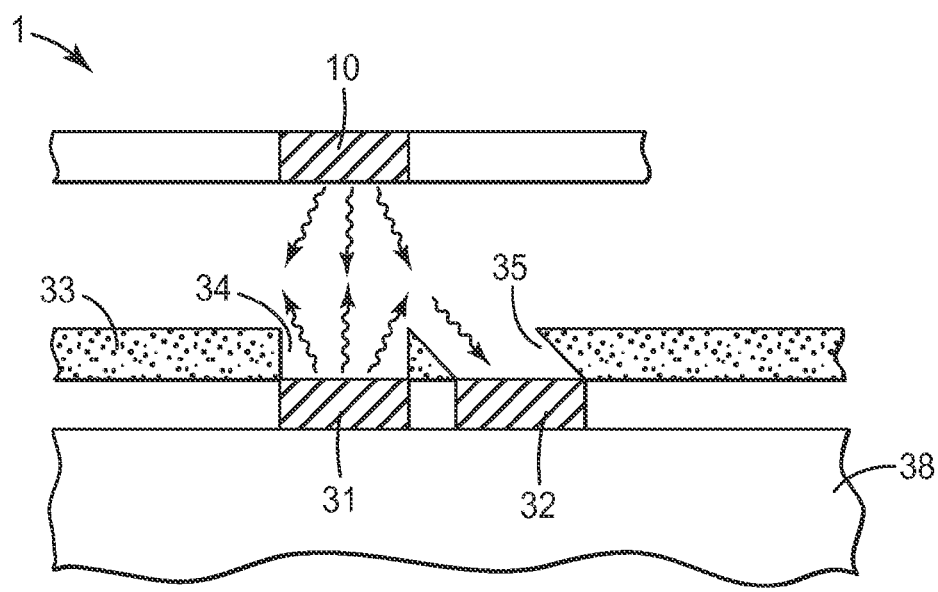
FIG. 4 is a side cross sectional view of an exemplary arrangement of a light source, a photodetector and sampling substrate.

In one embodiment, device 30 comprises at least one mated light source 31 and photodetector 32 pair that are configured so as to be able to optically interrogate at least one test zone 10 on substrate 1. Light source/photodetector pair 31/32 should be configured so as to be able to interrogate a given test zone 10 with adequate signal strength, accuracy, etc. Accordingly, light source 31 can be configured in device 30 so as to be able to be placed near to a test zone 10, such that at least a portion of the light output of source 31 can be directed toward test zone 10. With reference to FIGS. 3 and 4, in one embodiment light source 31 is positioned behind cover 33 of device 30, with cover 33 comprising an optically transmissive portion 34 (which may be a hole in cover 33) over source 31, such that light emitted from source 31 may be directed toward test zone 10.

Photodetector 32 can be configured in device 30 so as to be able to receive a reflected signal from test zone 10 upon the use of light source 31 to direct light onto test zone 10. For example, it may be useful to position photodetector 32 closely beside light source 31, as shown in the exemplary design of FIGS. 3 and 4. In various embodiments, photodetector 32 may be positioned at most about 5 mm, 10 mm, or 15 mm from light source 31. Additionally, it may be advantageous to mount light source 31 and photodetector 32 on a common printed circuit board 38, which may result in light source 31 and photodetector 32 being in a substantially coplanar configuration (as shown in FIG. 4). In such a case, photodetector 32 may also be placed behind cover 33 of device 30, with cover 33 comprising an optically transmissive portion 35 (which may be a hole in cover 33) over photodetector 32, such that at least a portion of light reflected from test zone 10 may be detected by photodetector 32.

In various embodiments, light source 31, photodetector 32, and/or optically transmissive portions 34 and/or 35, may be configured so as to most efficiently direct light from source 31 onto test zone 10, and collect reflected light therefrom by photodetector 32, while at the same time minimizing ambient light (or light from an adjacent light source) incident upon photodetector 32. Thus in an exemplary configuration in which photodetector 32 is positioned adjacent light source 31 and slightly off-axis relative to a direct path between light source 31 and test zone 10 (e.g., as shown in FIG. 4), optically transmissive portion 35 can be angled (as in FIG. 4), or can be made somewhat larger than the light-sensitive surface of photodetector 32 (e.g., as shown in FIG. 3), so as to not block any portion of the light that would otherwise reach photodetector 32. Similarly, optically transmissive portion 34 can be likewise configured, if desired.

Optically transmissive portions 34 and/or 35 can be optically transparent across substantially all of the visible light spectrum. Or, one or both portions 34/35 can include optical filters so as to block light of unwanted wavelengths while permitting the passage of light of desired wavelengths. Such filters can, in addition to being wavelength dependent, can be angle dependent (for example, so as to block ambient light).

Thus in summary, a light source/photodetector pair 31/32 may be configured such that upon the proper positioning of device 30 relative to sampling substrate 1, at least a portion of light emitted from source 31 can impinge upon a test zone 10, and at least a portion of light reflected from test zone 10 can be detected by photodetector 32. All, or even a substantial portion, of the light emitted by light source 31 does not necessarily have to be directed onto test zone 10. Likewise, photodetector 32 does not have to capture all, or even a substantial portion, of the light reflected from test zone 10. All that is necessary is that sufficient light is directed from light source 31 onto test zone 10, and sufficient reflected light therefrom is measured by photodetector 32, with sufficiently little interference from ambient light, such that a signal can be generated by photodetector 32 and processed as described herein, to allow an accurate indication of the oil quality to be generated.

The devices and methods disclosed herein may allow accurate interrogation via optical reflectance, with minimum use of space and with minimum expense, since they minimize the use of components such as fiber optic cables, lens arrays, filter wheels, and the like. In particular, devices and methods disclosed herein allow the production of a device 30 that may require few or no moving parts. Such a device 30 as disclosed herein may be much less expensive than devices such a spectrophotometers, optical densitometers, and the like.

In one embodiment (illustrated in FIGS. 1 and 3), device 30 comprises mated pairs of light sources/photodetectors 31a/32a, 31b/32b, etc., which mated pairs are spatially arranged such that they can be brought into proper alignment with test zones 10a, 10b, etc., respectively, so as to form a plurality of light source/photodetector/test zone sets, such that multiple test zones 10 of sampling substrate 1 can be interrogated without needing to move sampling substrate 1 and device 30 relative to each other. In the exemplary configuration shown in FIGS. 2 and 3, light sources 31 and photodetectors 32 are shown on the "bottom" of device 30; that is, on the major side of device 30 that is opposite the "top" side that has display screen 36. In addition to the terms top and bottom being used in their relative sense only, it should be understood that light sources 31 and photodetectors 32 may alternatively be positioned, for example, on the same side of device 30 as display 36 or within a cavity built into device 30. It should also be noted that the appearance of device 30 shown in FIG. 2 (a generally elongate appearance with two relatively flat major surfaces) is but one exemplary configuration. Many other configurations are possible; and, controls, display screens, light sources and/or photodetectors may be positioned on such a device in a wide variety of locations.

In optical monitoring, it may be useful to include referencing capability to take into account variations in temperature, varying output of light sources 31, varying response of photodetectors 32, background light levels, and the like. Accordingly, in various embodiments reference zones can be included in sample substrate 1 (in addition to the aforementioned test zones 10). Such reference zones may comprise materials that exhibit a known reflectance at various selected wavelengths or over selected wavelength ranges. As such, device 30 can comprise one or more additional light source/photodetector pairs that may be configured to interrogate such reference zones.

With particular regard to the possible effect of the temperature of the sampling substrate and/or the oil absorbed therein, on the reflectance signals, it is also possible to include an infrared temperature sensor in device 30, that is capable of determining the temperature of sampling substrate 10, if it is desired to adjust, correct, etc., the signal based on any effect of temperature.

In another embodiment, in addition to or in place of the inclusion of one or more reference zones on sampling substrates 1 that are used for oil sampling, reference strips may be provided that comprise one or more reference zones. In this case, the methods and devices disclosed herein may be configured such that a reference strip can be brought into proximity to device 30 such that light source/photodetectors pairs can measure reference zones of the reference strip, such that the performance of device 30 can be evaluated such that any necessary adjustments, recalibrations, etc. may be made. The methods and devices disclosed herein may also be configured such that a reference oil sample (that is, an oil sample comprising a known amount of free fatty acid) can be contacted with a sampling substrate (which may be a standard sampling substrate 1 or an above-described reference strip) such that device 30 interrogates one or more test zones 10 and/or reference zones. The results of this interrogation can be compared to the known value of free fatty acid in the reference oil sample, thus device 30 can be adjusted, calibrated, etc., as deemed necessary.

In one embodiment, the signal received by device 30 in such optical reflectance measurements is in the form of a voltage (for example, as generated by photodetector 32 in response to light incident on photodetector 32). That is, such a photodetector may convert an optical signal from test zone 10 to a signal such as voltage, that can then be manipulated, processed, etc. Device 30 can further comprise one or more analog to digital converters that can provide the voltage signal in a digital form for ease of processing by a microcontroller. In the case of multiple light sources 31, multiple test zones 10, and/or multiple photodetectors 32, a separate voltage signal will typically be provided by each photodetector 32 and which corresponds to each individual test zone 10 interrogated.

The inventors have found that, upon interrogation of a test zone 10 using methods and devices disclosed herein, a signal may be obtained therefrom. The inventors have further found that a signal resulting from use of a so-called white light LED light source in combination with a relatively broad-band photodiode photodetector (e.g. a signal reflecting the contributions of photons of various wavelengths) may exhibit sufficient change with the amount of free fatty acid in an oil sample, to be useful. Specifically, devices and methods as disclosed herein allow the detection of a change in the optical reflectance of a test zone 10 if the test zone is contacted by an oil which possesses greater than a threshold level of free fatty acid. (The specific threshold level of free fatty acid needed to trigger a response for a given test zone 10 can of course vary, e.g. depending on the amount of base included in the indicator/humectant/base mixture of that zone).

Figure 10:
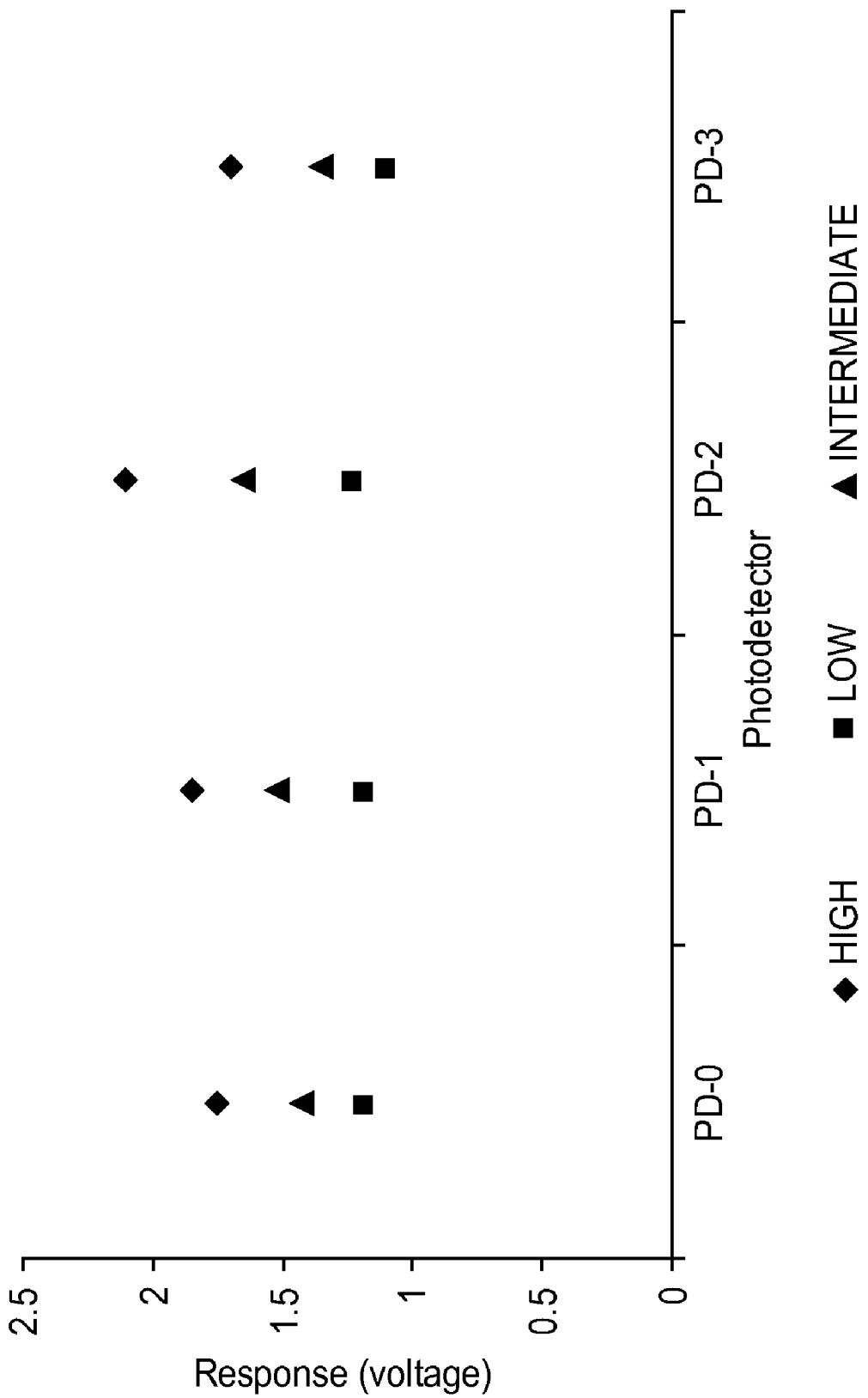
FIG. 10 is a plot of photodetector response to reflected light from sampling substrates under various conditions.

Upon exposure of a test zone 10 to an oil sample containing a free fatty acid level greater than the threshold level for that test zone, a change in optical reflectance of the test zone may be detected. By way of example, a test zone 10 as disclosed herein, when exposed to an oil sample containing a "low" level of free fatty acid (i.e., a level of free fatty acid below the threshold level for that test zone), may, when interrogated, result in a photodiode photodetector emitting a relatively "low" voltage signal (as seen, for example, in the data of FIG. 10). Such a condition will correspond generally to test zone 10 appearing blue upon visual inspection. Such a test zone when exposed to an oil sample containing a "high" level of free fatty acid (above the threshold level for that test zone), may, when interrogated, result in a photodiode photodetector emitting a relatively "high" voltage signal (as seen in FIG. 10). Such a condition will correspond generally to test zone 10 appearing yellow upon visual inspection.

In performing reflectance tests, the inventors have discovered that an "intermediate" level of free fatty acid may be detectable, which is not necessarily visually observable as a condition between "blue" and "yellow", but which nevertheless results in a photodiode detector emitting an "intermediate" signal (as shown in FIG. 10), which is intermediate between, and distinguishable from (by device 30), the "high" and "low" signals.

Thus in summary, through the methods and devices disclosed herein, the interrogation of a test zone 10 may be able to provide more information concerning the free fatty acid content of an oil sample than might otherwise be obtainable (e.g., by visual inspection). Such an ability to obtain more sensitive measurements of individual test zones 10 can be combined with the providing of multiple test zones 10 (which may comprise different levels of base thus may comprise different threshold levels of free fatty acid), so as to allow more accurate, sensitive, and/or precise evaluating of oil quality.

In generating an indication of the free fatty acid content based on interrogation of multiple test zones 10, device 30 may use signals received from all of the test zones (e.g., from all of the photodetectors 32). In a specific embodiment, device 30 uses (e.g. processes) a combined signal which is a combination of all of the signals from all of the photodetectors 32. In a particular embodiment, the signals from the various photodetectors are integrated (that is, summed or added together). The inventors have found that, upon exposure of multiple test zones 10 to oils containing various concentrations of free fatty acids, the integrated signal from the multiple photodetectors correlates well with the concentration of free fatty acid in the oil thus can be used by device 30 in providing an indication of the oil quality. The use of such an integrated signal, in combination with the fact that each photodetector may be capable of providing a signal corresponding to detection of an "intermediate" level of free fatty acid, may provide improved accuracy, for example without having to use an impractically large number of individual test zones 10.

Figure 5:
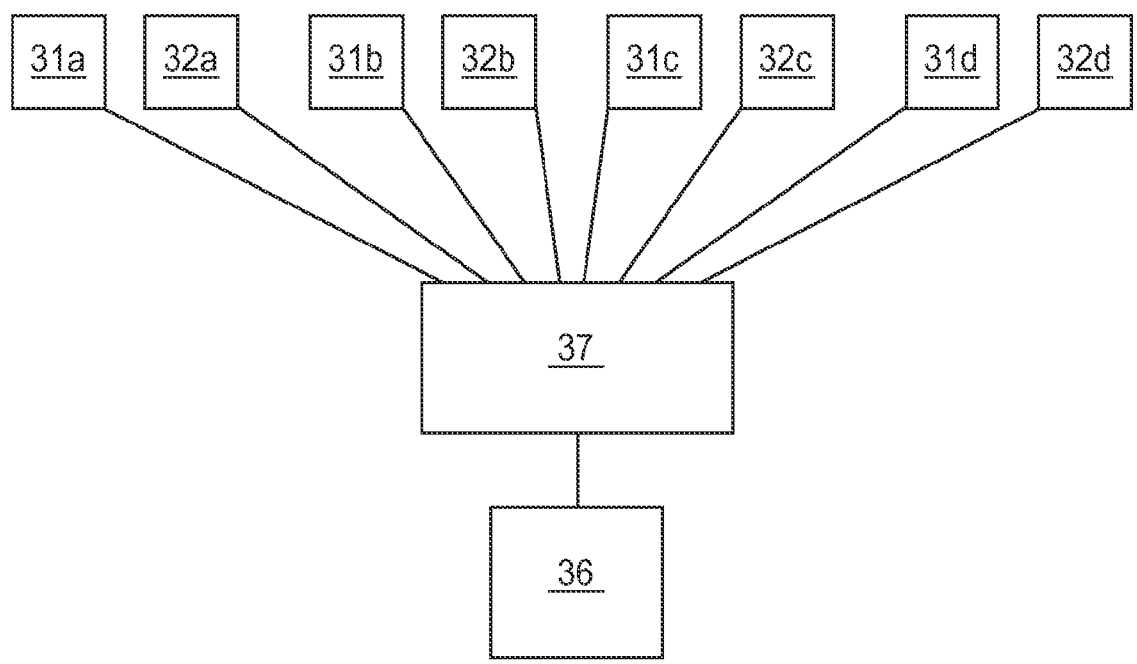
FIG. 5 is a block diagram of one embodiment of an optical interrogation device.

Aside from the above-mentioned integration step, the signals received from the various test zones 10 can be mathematically manipulated (individually or in combination) according to algorithms resident in the circuitry of device 30 (e.g., loaded into software or firmware) as desired. Thus, device 30 may comprise such components, circuitry, etc., as needed to perform such desired signal processing, and also as needed to control light sources 31 and/or photodetectors 32, and so on. With reference to the block diagram of FIG. 5, device 30 may comprise microcontroller 37 that can operate light sources 31, can operate (and receive signals from) photodetectors 32, can process, manipulate, etc., signals received from photodetectors 32, can hold various data and parameters in memory, can communicate with display 36, can receive input from a user of device 30, and can carry out other functions as needed. In a particular embodiment, device 30 can comprise the type of microcontroller known as a PIC (variously known as a Programmable Interface Controller, or Programmable Intelligent Computer), which may be particularly suited for the uses described herein. The various components of device 30 (light sources 31, photodetectors 32, display screen 36, microcontroller 37, and other components as described below) can be connected to, and/or physically mounted on, one or more printed circuit boards. Device 30 can have various other features, such as a keypad, buttons or a touch-screen interface for inputting information, power sources (e.g. battery or electric cord), and the like.

If it is found that certain types of oil display a different signal when interrogated according to the devices and methods disclosed herein (e.g., independent of the amount of free fatty acid in the oil), device 30 can include a mechanism wherein a user can input the identity (type) of the oil being tested, so that device 30 can automatically adjust or compensate based on the type of oil. In addition, it is also possible to configure device 30 such that, when a new batch of oil is introduced for cooking, the oil is tested so as to obtain a baseline (reference) reflectance signal which can be stored within the memory of device 30 and which corresponds to that particular type and/or batch of oil. This stored baseline signal can then be used when the oil is interrogated later, so that device 30 can automatically adjust or compensate based on the particular characteristics of that batch of oil.

Thus in summary, interrogation device 30 will, from signals received and/or processed as described above, produce an indication of the oil quality of an oil sample, the indication being associated with (e.g., based on) the free fatty acid content of the oil sample. The indication can be communicated to a user of device 30 (for example, by a visual or audio signal). In one embodiment, the indication can be an actual numerical value of the free fatty acid content. Alternatively, the indication can be a parameter that, while not a numerical value of the free fatty acid content, is associated with the free fatty acid content and can serve to allow the user to ascertain the quality of the oil (e.g., whether the oil is still suitable for use). For example, device 30 may have a screen 36 on which is presented a bar graph, the height of which is representative of the amount of free fatty acid. Or, a set or sets of signals (e.g., red, yellow, and green lights) may be may be used to indicate the quality of the oil in terms of free fatty acid content. Or, device 30 may present oil quality information to the user in a binary (pass/fail) format by (e.g., by way of an audio or visual signal) based on the free fatty acid content.

In producing such an indication, it may be helpful if device 30 comprises information (e.g., stored in electronic memory, firmware or software, for example in a lookup table) which allows device 30 to correlate the aforementioned combined (e.g., integrated) signal with the free fatty acid content of the oil. Such information can be resident in the electronic memory of device 30 as a fixed value. Or, such information can be periodically updated and/or changed, e.g. by using device 30 to interrogate one or more standard materials with known amounts of free fatty acid, and/or with known reflectance properties (e.g. reference zones, reference strips, reference oil samples, etc).

Device 30 may be constructed in such a manner that a sampling substrate 1 can be interrogated with the sampling substrate in the open, e.g. lying on a counter, held by hand, etc. If it is useful to minimize the effect of stray or background light, various methods may be employed so as to achieve this. For example, device 30 may be constructed so as to comprise a partially or substantially enclosed chamber (not shown in any figure) such that sampling substrate 1 can be placed inside the chamber for interrogation. This can be done, for example, by providing a cavity inside device 30, which contains light sources 31 and photodetectors 32, and into which sampling substrate 10 can be inserted; or, a cover (e.g., a hinged cover, slidable cover, etc.) can be provided such that the cover can be positioned so as to block ambient light, after sampling substrate 10 is placed in position for interrogation. In particular, if sampling substrate 1 is to be interrogated while positioned on a surface (e.g., while lying on a table), device 30 can comprise a skirt or flange (not shown in any figure) that, when brought near to the surface or placed into contact with it, forms a partially or substantially enclosed chamber.

In various embodiments it may be desired to achieve registration (alignment) between sampling substrate 1 and device 30 for best functioning. That is, it may be desired to accurately position sampling substrate 1 relative to device 30 such that test zones 10 are aligned with light sources 31 and photodetectors 32 to provide the most accurate optical interrogation. Such registration may be achieved in a variety of ways. For example, a physical registration method may be used wherein an edge or other portion of sampling substrate 1 is positioned against, or held within, a holder (e.g. a clip, post, stub, etc) which may be provided on the interrogation device 30 itself or on a separate holding fixture.

Registration can also be achieved by optical means rather than by physical methods. Thus, sampling substrate 1 can have one or more features that can be recognized by the user and/or by device 30 for purposes of registration. For example, sampling substrate 1 can comprise an indicia that may be used by the user in achieving proper registration of sampling substrate 1 relative to device 30. Or, device 30 may comprise optical recognition capability so as to be able to recognize such an indicia. In such a case, upon detection by device 30 of adequate registration with sampling substrate 1, device 30 can notify a user (e.g. by means of an optical signal, an audible signal, etc.) that the device is ready to interrogate sampling substrate 1. Alternatively, device 30 may be configured such that optical interrogation proceeds automatically upon device 30 recognizing that adequate registration has been achieved.

EXAMPLES

Example 1

Test strips were obtained that are available from 3M Company under the designation 3M Shortening Monitor Test Strips, and that are believed to be manufactured in similar manner to methods described in U.S. Pat. No. 4,654,309, Example 4.

Cooking oil was obtained that had a composition of approximately 40% sunflower oil (minimum 70% oleic acid), approximately 30% palm oil, and approximately 30% hydrogenated rapeseed oil (all percentages by weight). The cooking oil was used in cooking french fries for a period of about two months, over which time small samples were periodically removed from the oil.

The samples were tested by the following procedure. Since most of the samples were solid at room temperature, each sample (150 cc in plastic jars) was heated in a microwave oven for 60 seconds or until the sample melted to form a liquid. A test strip was then dipped into the oil sample, then placed onto a paper towel to remove any excess oil. The optical reflectance of each of the four test zones of the strip (i.e., the zones that were blue in appearance as the strip was received) was then measured using a QuadScan Reflectance Photometer (Model 100, available from KGW Enterprises, Elkhart, Ind.). Optical filters were used so as to interrogate the zones at specific wavelength ranges: the blue wavelength corresponded to a wavelength range of approximately 400-510 nm, the green wavelength 510-586 nm, the red wavelength 586-660 nm, and the infrared (IR) wavelength 825-855 nm.

The optical reflectance of the four test zones was measured by traversing the test strip relative to the reflectance photometer such that the interrogation unit of the photometer interrogated each of the test zones in succession. (Readings were taken over the entire test strip, including blank areas between the test zones, but readings from the blank areas in between the test zones were not used.) The strip was shielded from ambient light during this process. Typically, for each strip the reflectance readings from the four test zones were averaged together. Thus, in the plots of FIGS. 6-9, each data point typically represents the averaged reflectance of four test zones of a test strip.

For the various oil samples, the free fatty acid concentration was estimated, by standard (visual) use of 3M Shortening Monitor Strips in accordance with the product instructions. According to the product instructions, visually obtained results will fall into one of the following categories: free fatty acid content of less than 2%; free fatty acid content of 2% to less than 3.5%; free fatty acid content of 3.5% to less than 5.5%; free fatty acid content of 5.5% to less than 7%; or, free fatty acid content of greater than 7%. Plots (FIGS. 6-9) were then produced in which the measured reflectance (obtained via interrogation in different wavelength ranges) was plotted against the free fatty acid content as estimated by visual use of the product. Within these general groupings of data (e.g., within the group with 3.5-5.5% free fatty acid content, the group with 5.5-7.0% free fatty acid content, etc.) it was also possible to at least qualitatively rank the individual oil samples according to their estimated free fatty acid content. This could be done, for example, according to the known length of time that a particular oil sample had been in use (which would be expected to increase the free fatty acid content); or, according to the content of total polar compounds in the sample, as measured according to method ISO 8420 (of which free fatty acids comprise a portion and thus would be expected to at least generally correlate with); or, according to the brightness or intensity of the visually observed test zones. Thus, within the general groupings of the data in FIGS. 6-9, the data within each grouping are arranged such that samples with lower estimated free fatty acid content are toward the left hand side of the group, and samples with higher estimated higher free fatty acid content are toward the right hand side of the grouping. No attempt at quantification of specific concentrations of free fatty acid should be inferred, however.

Figure 6:
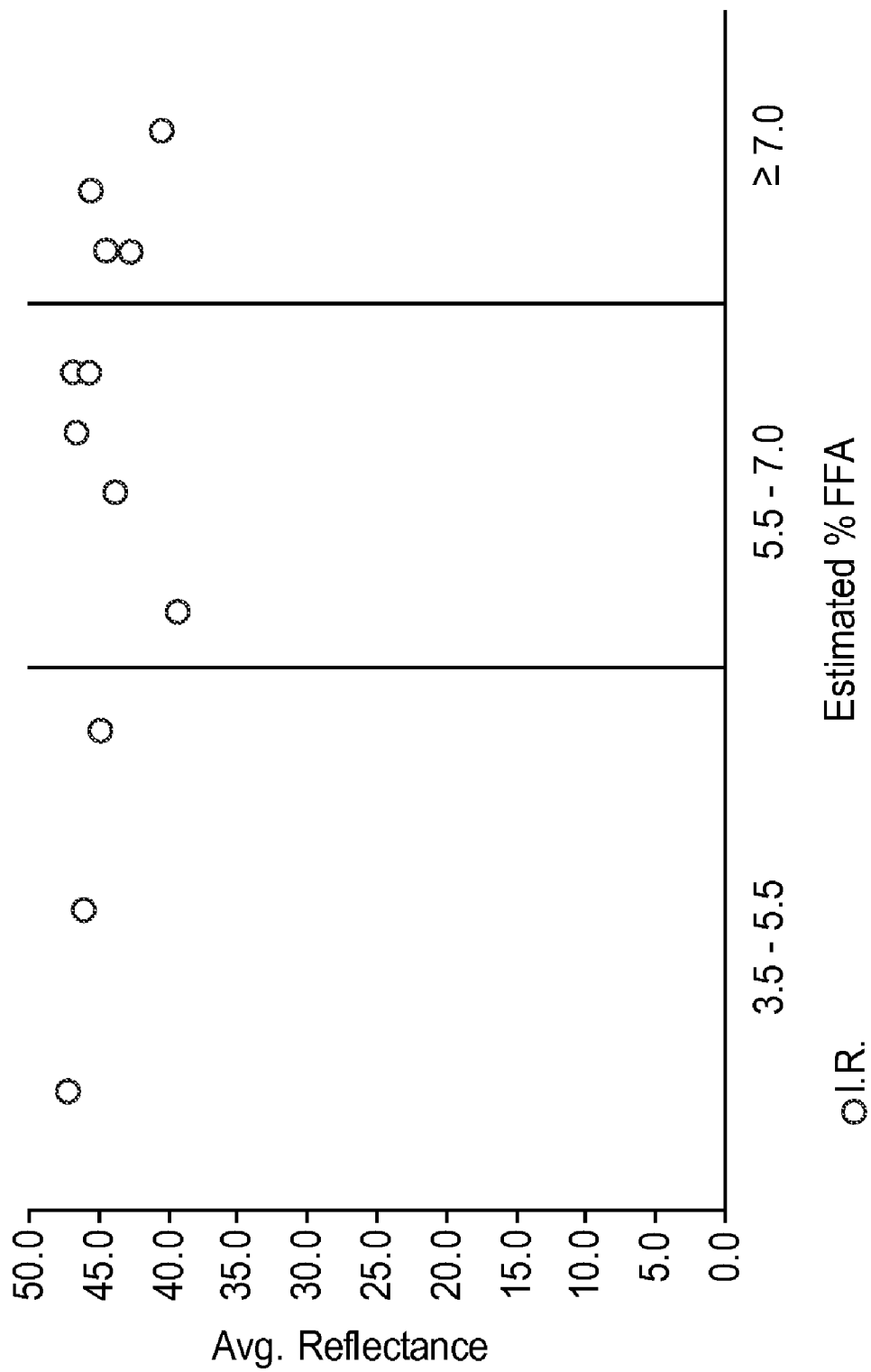
FIG. 6 is a plot of optical reflectance of sampling substrates comprising oil samples of various free fatty acid concentrations.
Figure 7:
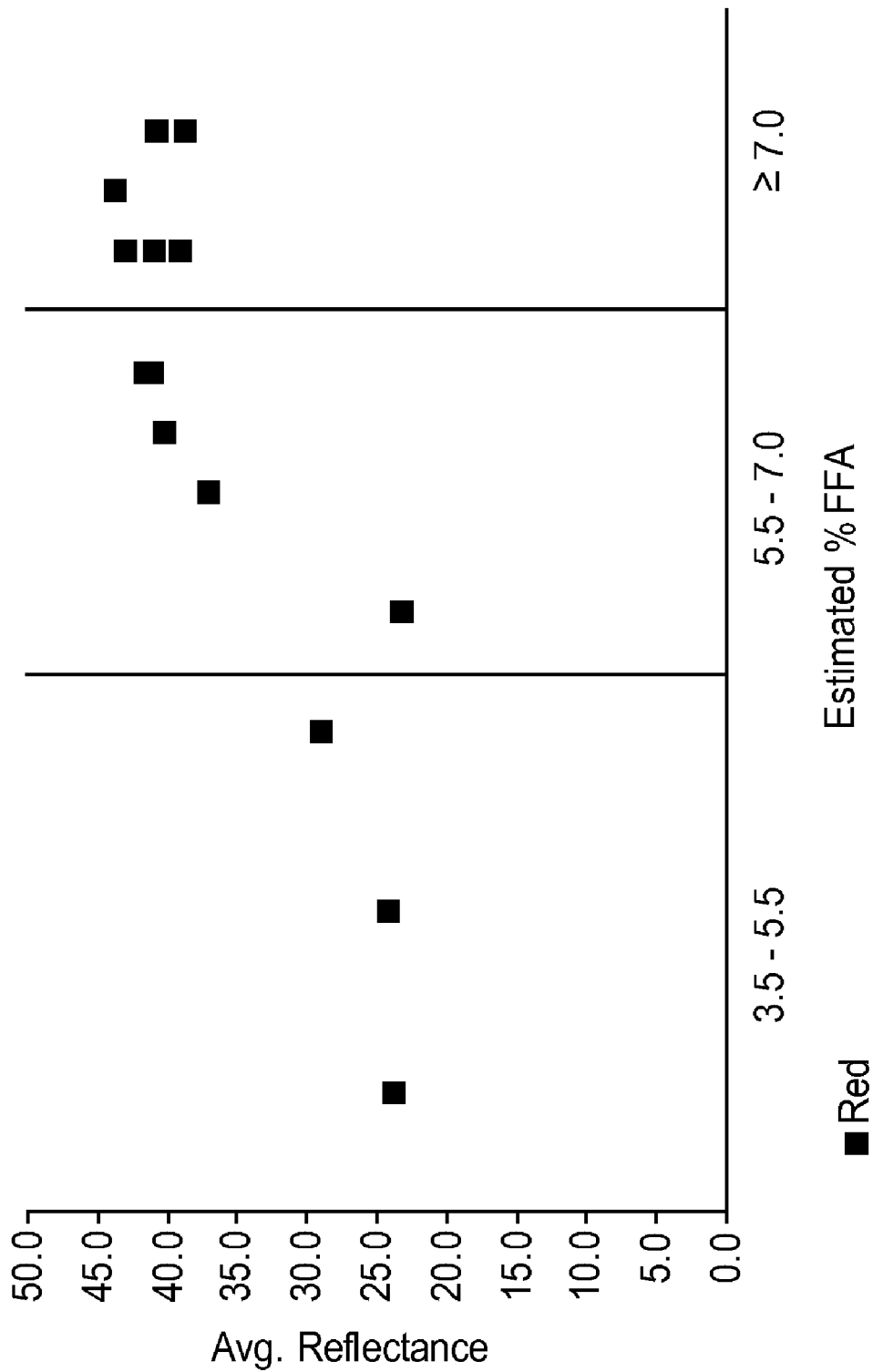
FIG. 7 is a plot of optical reflectance of sampling substrates comprising oil samples of various free fatty acid concentrations.
Figure 8:
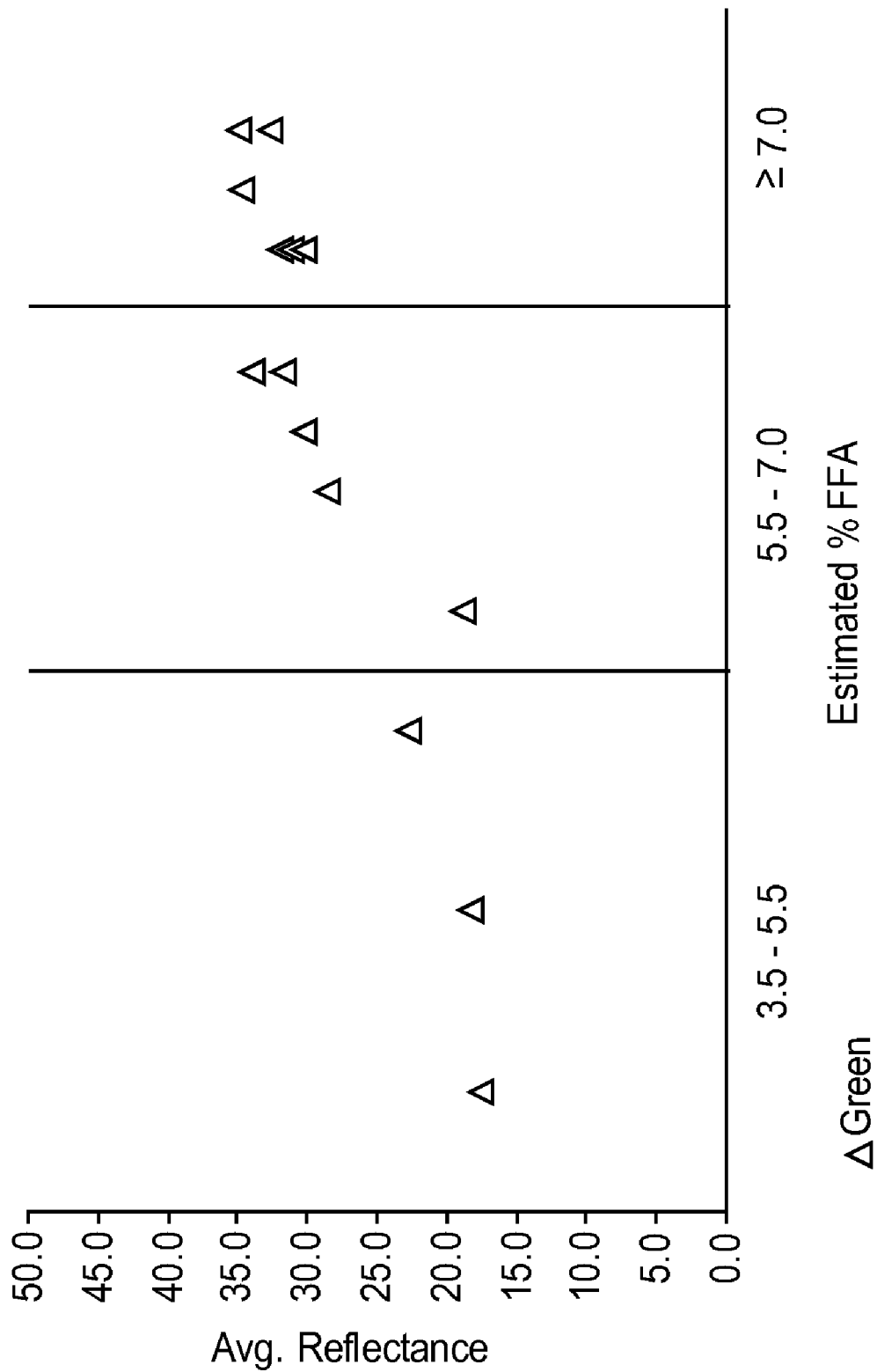
FIG. 8 is a plot of optical reflectance of sampling substrates comprising oil samples of various free fatty acid concentrations.
Figure 9:
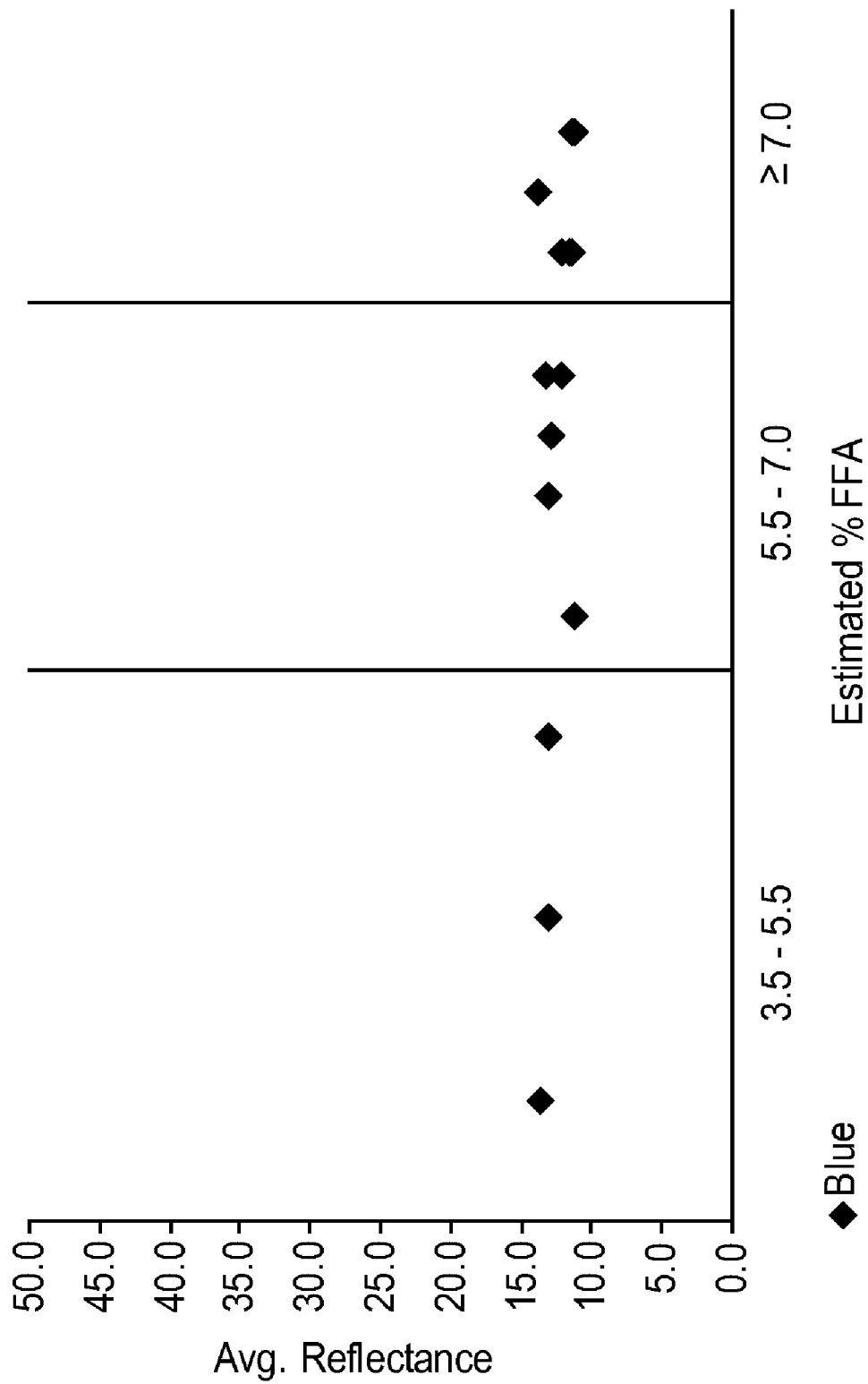
FIG. 9 is a plot of optical reflectance of sampling substrates comprising oil samples of various free fatty acid concentrations.

For convenience of presentation, the data is broken up into four plots. FIG. 6 contains data from interrogation in the infrared wavelength range; FIG. 7 contains data from interrogation in the red wavelength range; FIG. 8, green; and FIG. 9, blue. In general, the reflectance data indicates that, in these experiments, interrogation in the red or green wavelength range provided a larger response than did interrogation in blue or infrared wavelength range.

Example 2

Test strips were obtained that are available from 3M Company under the designation 3M Shortening Monitor Test Strips, and that are believed to be manufactured in similar manner to methods described in U.S. Pat. No. 4,654,309, Example 4.

Four photodetector photodiodes (type Si PIN) were obtained from Hamamatsu Photonics, Hamamatsu City, Japan, under the designation S9345. The individual photodiodes were labeled PD-0, PD-1, PD-2, and PD-3.

Light emitting diodes (type Super-White (GaN) were obtained from SuperBright LEDs, Inc, of St. Louis, Mo., under the designation RL5-W5020.

Test strips were obtained that are available from 3M Company under the designation 3M Shortening Monitor Test Strips, and that are believed to be manufactured in similar manner to methods described in U.S. Pat. No. 4,654,309, Example 4.

Test zones from various test strips were contacted with oil samples containing a "Low" amount of free fatty acid; that is, an amount that, for these test zones, would not trigger a visual change (blue color to yellow color) noticeable to a typical human user. The test zones were then interrogated by way of directing light from the LEDs onto the test zones, and measuring reflected light therefrom by way of the photodiodes (with the LEDs and photodiodes being configured and operated in accordance with manufacturers recommendations and by methods well known in the art). For the four individual photodiodes, the resulting output voltage is presented in FIG. 10 (labeled "Low Free Fatty Acid").

Other test zones were contacted with oil samples containing a "High" amount of free fatty acid; that is, an amount that, for these test zones, would trigger a visual change (blue color to yellow color) noticeable to a typical human user. The test zones were then interrogated by use of the LEDs and the photodiodes as described above, with the resulting output voltage from the photodiodes presented in FIG. 10 (labeled "High Free Fatty Acid").

Other test zones were contacted with oil samples containing a "Medium" amount of free fatty acid. This was believed to be an amount that, for these test zones, might not reliably trigger a visual change (blue color to yellow color) noticeable to a typical human user. The test zones were then interrogated by use of the LEDs and the photodiodes as described above, with the resulting output voltage from the photodiodes presented in FIG. 10 (labeled "Medium Free Fatty Acid").

As presented in FIG. 10, interrogation of test zones using the methods and apparatus described above, allowed the obtaining of an "intermediate" signal which could be distinguished from a signal corresponding to a "low" state (i.e. a state in which the test zones appeared visually blue), and from a signal corresponding to a "high" state (i.e. a state in which the test zone appeared visually yellow).

The tests and test results described above are intended solely to be illustrative, rather than predictive, and variations in the testing procedure can be expected to yield different results. The foregoing detailed description and examples have been given for clarity of understanding only. No unnecessary limitations are to be understood therefrom. In particular, headings and/or subheadings in this disclosure are provided for convenience of reading, and no unnecessarily limitations are to be understood therefrom.

The present invention has now been described with reference to several embodiments thereof. It will be apparent to those skilled in the art that changes can be made in the embodiments described without departing from the scope of the invention. Thus, the scope of the present invention should not be limited to the exact details and structures described herein, but rather by the structures described by the language of the claims, and the equivalents of those structures.

The invention claimed is:

1. A method of evaluating the quality of frying oil, the method comprising the steps of:
   providing frying oil that potentially comprises free fatty acid content;
   providing an oil-absorbent sampling substrate, wherein the sampling substrate contains a plurality of test zones, wherein each test zone is responsive to free fatty acid;
   contacting the oil with the sampling substrate such that a sample of the oil is brought into contact with at least a portion of each of the test zones;
   directing light onto the plurality of test zones;
   measuring the amount of light reflected from each test zone;
   generating signals proportional to the amount of light reflected from each test zone;
   summing the signals together so as to provide an integrated signal;
   correlating the integrated signal with the free fatty acid content of the oil; and
   reporting an indication of the oil quality of the oil by an optical interrogation device, wherein the indication is associated with the free fatty acid content of the oil.

2. The method of claim 1 wherein a separate light source is used to direct light on each test zone.

3. The method of claim 2 wherein at least one of the separate light sources is a broadband light-emitting diode.

4. The method of claim 2 wherein at least one of the separate light sources is a light-emitting diode that emits light in the green wavelength range of from about 510 nm to about 586 nm.

5. The method of claim 2 wherein at least one of the separate light sources is a light-emitting diode that emits light in the red wavelength range of from about 586 nm to about 660 nm.

6. The method of claim 1 wherein a separate photodetector is used to detect light reflected from each test zone.

7. The method of claim 6 wherein the separate photodetectors are photodiodes.

8. A method of evaluating the quality of frying oil, the method comprising the steps of:
   providing an interrogation device that comprises a plurality of light source and photodetector pairs;
   providing an oil-absorbent sampling substrate,
   wherein the sampling substrate contains a plurality of test zones,
   wherein each test zone is responsive to free fatty acid;
   providing frying oil that potentially comprises free fatty acid content;
   contacting the oil with the sampling substrate such that a sample of the oil is brought into contact with at least a portion of each of the test zones;
   positioning the interrogation device and the sampling substrate such that each light source and photodetector pair is placed in proximity to a test zone, so as to provide a plurality of light source, photodetector, and test zone sets;
   for each light source, photodetector, and test zone set, directing light onto the test zone from the light source and measuring reflected light therefrom by the photodetector and generating a signal that is proportional to the measured reflected light;
   combining the signals from the photodetectors so as to provide a combined signal;
   correlating the combined signal with the free fatty acid content of the oil based on information stored in the interrogation device; and
   reporting an indication of the oil quality of the oil, wherein the indication is associated with the free fatty acid content of the oil.

9. The method of claim 8 wherein combining the signals comprises summing the signals together to form an integrated signal.

10. The method of claim 8 wherein each light source and photodetector pair comprises a light source and a photodetector that are positioned within at most 10 mm from each other.

11. The method of claim 10 wherein for each light source and photodetector pair, the light source and the photodetector are positioned in a coplanar configuration and are mounted on a common circuit board.

12. The method of claim 11 wherein all of the light sources and photodetectors in the interrogation device are mounted on a common circuit board.

13. The method of claim 8, wherein the light source and photodetector pairs in the interrogation device are spatially arranged so as to correspond to the spatial arrangement of the test zones on the sampling substrate.

14. The method of claim 13 wherein, upon positioning the interrogation device and the sampling substrate such that each light source and photodetector pair is placed in proximity to a test zone, all of the test zones are interrogated without moving the sampling substrate and the interrogation device relative to each other.

15. The method of claim 8 including the step in which the interrogation device verifies that the sampling substrate is compatible with the interrogation device.

16. A system for evaluating the quality of frying oil, the system comprising:
- an oil-absorbent sampling substrate, wherein the sampling substrate contains a plurality of test zones, wherein each test zone is responsive to free fatty acid; and
- an optical interrogation device that comprises a plurality of light source and photodetector pairs;
- wherein the interrogation device and the sampling substrate are configured such that each light source and photodetector pair can be placed in proximity to a test zone, so as to provide a plurality of light source, photodetector, test zone sets;
- wherein the interrogation device and the sampling substrate are further configured such that, for each light source, photodetector, and test zone set, each test zone can be optically interrogated by the light source and photodetector pair so as to receive a signal therefrom, without moving the interrogation device and the sampling substrate relative to each other; and
- wherein the interrogation device comprises means to combine the signals received from the test zones into a combined signal, means to correlate the combined signal with the free fatty acid content of the oil, and means to report an indication of the oil quality of the oil, wherein the indication is associated with the free fatty acid content of the oil.

17. The system of claim 16 wherein the sampling substrate comprises a mark.

18. The system of claim 17 wherein the mark can be identified by the interrogation device and the presence of the mark used by the interrogation device to verify that the sampling substrate is compatible with the interrogation device.

19. The system of claim 17 wherein the mark can be used by the interrogation device to determine whether the sampling substrate is aligned correctly with the interrogation device such that the test zones are in proximity to the light source/photodetectors pairs such that the test zones can be interrogated.

20. The system of claim 16 wherein all of the light sources and photodetectors in the interrogation device are mounted on a common circuit board.

* * * * *